(12) United States Patent
Lee et al.

(10) Patent No.: US 12,422,300 B2
(45) Date of Patent: Sep. 23, 2025

(54) WEIGHING SYSTEM

(71) Applicants: ASTEK TECHNOLOGY LTD., Tainan (TW); CHI MEI MEDICAL CENTER, Tainan (TW)

(72) Inventors: Ying-Li Lee, Tainan (TW); Jiun-Hung Lin, Tainan (TW); Chun-Hao Lu, Tainan (TW); Yen-Jung Lu, Tainan (TW); Chia-Chen Hsu, Tainan (TW); Chih-Yi Li, Tainan (TW); Ching-Yu Lee, Tainan (TW); Chia-Chi Chang, Tainan (TW); Ya-Wen Kung, Tainan (TW); Li-Chien Yang, Tainan (TW); Huey-Jeng Yang, Tainan (TW)

(73) Assignees: ASTEK TECHNOLOGY LTD. (TW); CHI MEI MEDICAL CENTER (TW)

( * ) Notice: Subject to any disclaimer, the term of this patent is extended or adjusted under 35 U.S.C. 154(b) by 298 days.

(21) Appl. No.: 18/231,087

(22) Filed: Aug. 7, 2023

(65) Prior Publication Data

US 2024/0053190 A1 Feb. 15, 2024

(30) Foreign Application Priority Data

Aug. 12, 2022 (TW) .................................. 111130448

(51) Int. Cl.
*G01G 23/42* (2006.01)
*G01G 19/50* (2006.01)
*G16H 10/60* (2018.01)

(52) U.S. Cl.
CPC .............. *G01G 23/42* (2013.01); *G01G 19/50* (2013.01); *G16H 10/60* (2018.01)

(58) Field of Classification Search
CPC ........ G01G 23/18; G01G 19/00; G01G 23/42; G01G 19/50; G01G 19/4146; G06F 16/25;

(Continued)

(56) References Cited

U.S. PATENT DOCUMENTS 5,000,274 A * 3/1991 Bullivant ............. G07G 1/0054
177/128
8,727,883 B2 * 5/2014 Pelkey .................. H04L 51/046
463/42

(Continued)

FOREIGN PATENT DOCUMENTS

CN 216623777 U 5/2022
TW M592074 U 3/2020

OTHER PUBLICATIONS

Search Report appended to an Office Action, which was issued to Taiwanese counterpart application No. 111130448 by the TIPO on Jul. 20, 2023, with an English translation thereof. (2 pages).

*Primary Examiner* — Jacques M Saint Surin
(74) *Attorney, Agent, or Firm* — DLA PIPER LLP (US); Blake W. Jackson

(57) ABSTRACT

A system includes a processor, and a display, a reader, a switch, a scale, a memory device, intake-type buttons and output-type buttons that are connected to the processor. The processor controls the display to display an identification number obtained by using the reader to read an identifier. The switch is operated to enable the processor to operate in an intake mode or an output mode. When operating in the intake (output) mode, the processor controls the display to display a symbol corresponding to one of the intake-type (output-type) buttons that is determined to be pressed, and in response to receipt of weight data from the scale, controls the display to display a value of pre-intake (post-output) weight obtained based on the weight data, and stores the value of pre-intake (post-output) weight in the memory device.

18 Claims, 13 Drawing Sheets

(58) Field of Classification Search
CPC .. G06F 3/147; G06F 16/2462; G06F 17/0022; G16H 50/20; G16H 40/63; G16H 50/70; G16H 10/60; G16H 40/67
See application file for complete search history.

(56) References Cited

U.S. PATENT DOCUMENTS

| | | | | |
|---|---|---|---|---|
| 8,822,847 B2* | 9/2014 | Vidal | ................... | G01G 19/414 |
| | | | | 128/923 |
| 2014/0353049 A1* | 12/2014 | Vidal | ................... | G01G 19/414 |
| | | | | 177/25.13 |

* cited by examiner

WEIGHING SYSTEM

CROSS-REFERENCE TO RELATED APPLICATION

This application claims priority to Taiwanese Invention Patent Application No. 111130448, filed on Aug. 12, 2022.

FIELD

The disclosure relates to a weighing system, and more particularly to a weighing system that facilitates keeping a nursing record for a subject.

BACKGROUND

In clinical practice, for a patient who is hospitalized, a nurse has to keep a nursing record for this patient. The nursing record contains information of intake and output (I&O), which is related to the measure of intake substances (e.g., food, drinking water, drugs, nutritional supplements, juice, blood products or the like) entering the body of the patient and output substances (e.g., feces, urine or the like) leaving the body of the patient. Conventionally, the nurse has to measure the weights of the intake substances by using a weight scale, and measure weights of the output substances by using another weight scale, and write down the weights of the these substances in the nursing record. Such process involves a great amount of manual operation by the nurse, and thus is prone to human errors.

SUMMARY

Therefore, an object of the disclosure is to provide a weighing system for facilitating keeping a nursing record for a subject that can alleviate at least one of the drawbacks of the prior art.

According to the disclosure, the subject being assigned an identification number that is stored by an identifier. The weighing system includes a reader, a weight scale, a processor, a mode switch, a display, a memory device, an intake-type button set and an output-type button set.

The reader is configured to read the identifier to obtain the identification number of the subject.

The weight scale is configured to support an object, to measure weight of the object, and to output an entry of weight data indicating the weight of the object currently measured.

The processor is disposed in the weight scale, is electrically connected to the reader and the weight scale, and is configured to receive the identification number of the subject from the reader, to receive the entry of weight data from the weight scale, and to operate in one of an intake mode and an output mode.

The mode switch is disposed on the weight scale, is electrically connected to the processor, and is configured to be operated to enable the processor to operate in one of the intake mode and the output mode.

The display is disposed on the weight scale, is electrically connected to the processor, and is configured to be controlled by the processor to display the identification number of the subject.

The memory device is disposed in the weight scale, and is electrically connected to the processor.

The intake-type button set is disposed on the weight scale, is electrically connected to the processor, and includes a plurality of intake-type buttons respectively corresponding to a plurality of intake-type visual symbols that are respectively related to a plurality of types of intake substances.

The output-type button set is disposed on the weight scale, is spaced apart from the intake-type button set, is electrically connected to the processor, and includes a plurality of output-type buttons respectively corresponding to a plurality of output-type visual symbols that are respectively related to a plurality of types of output substances.

When operating in the intake mode, the processor is further configured to determine whether any one of the intake-type buttons and the output-type buttons is pressed. When it is determined that one of the intake-type buttons is pressed, the processor is further configured to control the display to display one of the intake-type visual symbols that corresponds to the one of the intake-type buttons, and in response to receipt of the entry of weight data from the weight scale, to obtain a value of pre-intake weight based on the entry of weight data, to control the display to display the value of pre-intake weight, and to store the value of pre-intake weight in the memory device. When it is determined that one of the output-type buttons is pressed, the processor is further configured to not control the display to display any one of the output-type visual symbols.

When operating in the output mode, the processor is further configured to determine whether any one of the intake-type buttons and the output-type buttons is pressed. When it is determined that one of the output-type buttons is pressed, the processor is further configured to control the display to display one of the output-type visual symbols that corresponds to the one of the output-type buttons, and in response to receipt of the entry of weight data from the weight scale, to obtain a value of pre-output weight based on the entry of weight data, to control the display to display the value of pre-output weight, and to store the value of pre-output weight in the memory device. When it is determined that one of the intake-type buttons is pressed, the processor is further configured to not control the display to display any one of the intake-type visual symbols.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
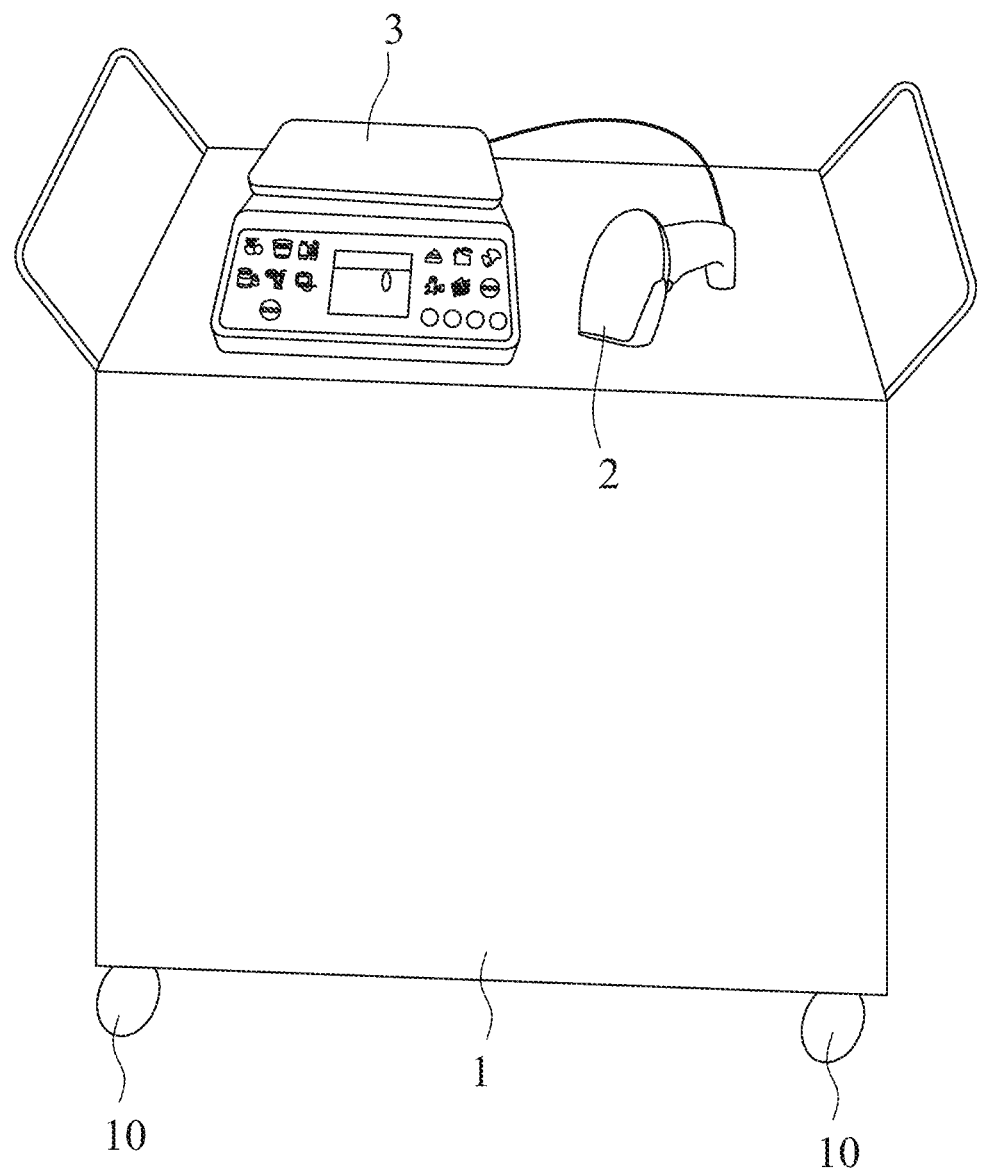
FIG. 1 is a perspective view illustrating a weighing system according to an embodiment of the disclosure.
Figure 2:
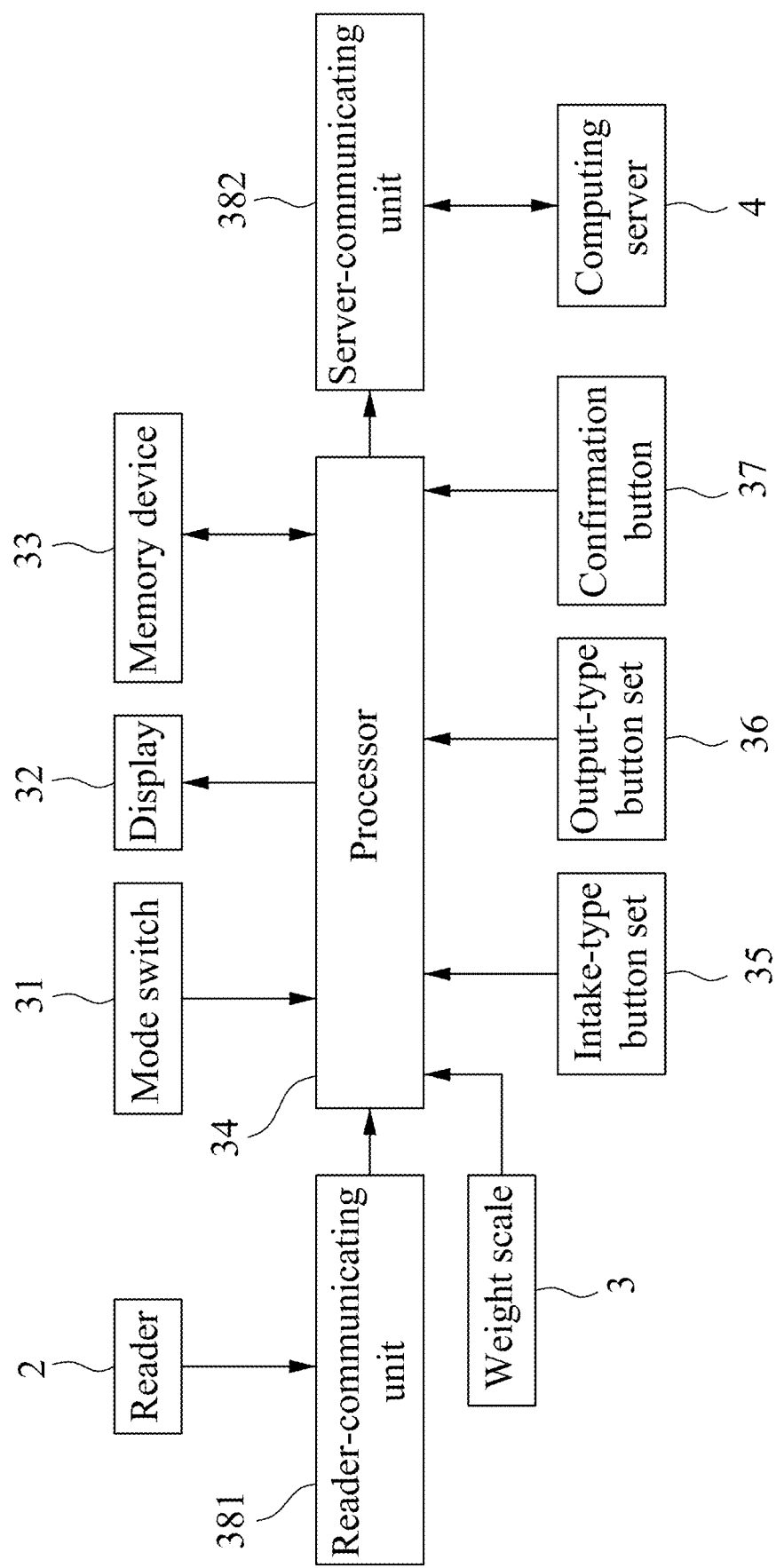
FIG. 2 is a block diagram illustrating the weighing system according to the embodiment of the disclosure.

Referring to FIGS. 1 to 5, an embodiment of a weighing system that facilitates keeping a nursing record for a subject according to the disclosure is illustrated. The subject may be a patient, but is not limited thereto. The subject is assigned an identification number that is stored by an identifier. The identification number is exemplarily a patient number 320 (e.g., "87654321" as shown in FIG. 6), but is not limited thereto. The identifier may be implemented by a barcode or a radio frequency identification (RFID) tag, but is not limited thereto. In this embodiment, the identifier is disposed on a wristband worn on a wrist of the subject, but is not limited thereto.

The weighing system includes a reader 2, a weight scale 3, a mode switch 31, a display 32, a memory device 33, a processor 34, an intake-type button set 35, an output-type button set 36, a confirmation button 37, a reader-communicating unit 381, a server-communicating unit 382, a computing server 4 and a mobile cart 1. The weighing system further includes a power supply having a connection port 380 (e.g., a USB port). The power supply is configured to receive mains electricity via a power cable connected to the connection port 380, to store electricity, and to supply electricity to the reader 2, the weight scale 3, the display 32, the memory device 33, the processor 34, the reader-communicating unit 381, the server-communicating unit 382 and so on.

The mobile cart 1 includes a plurality of wheels 10 as shown in FIG. 1. The mobile cart 1 is configured to support the reader 2 and the weight scale 3, and to carry the reader 2 and the weight scale 3 to move together with the mobile cart 1.

The reader 2 is configured to read the identifier to obtain the identification number of the subject. In one embodiment where the identifier is a barcode, the reader 2 is implemented by a barcode scanner. In one embodiment where the identifier is an RFID tag, the reader 2 is implemented by an RFID reader.

Figure 3:
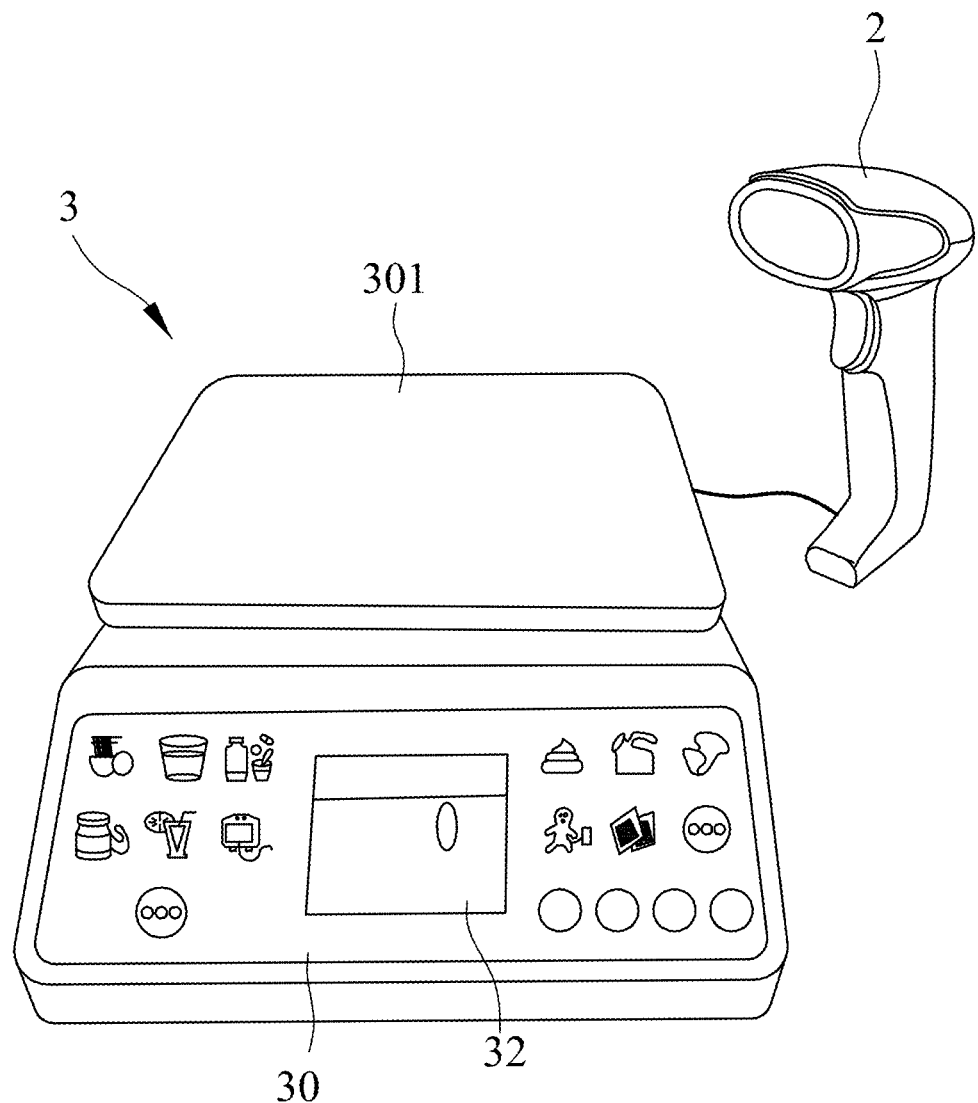
FIG. 3 is a perspective view illustrating an example of a weight scale and a reader of the weighing system according to the embodiment of the disclosure.
Figure 4:
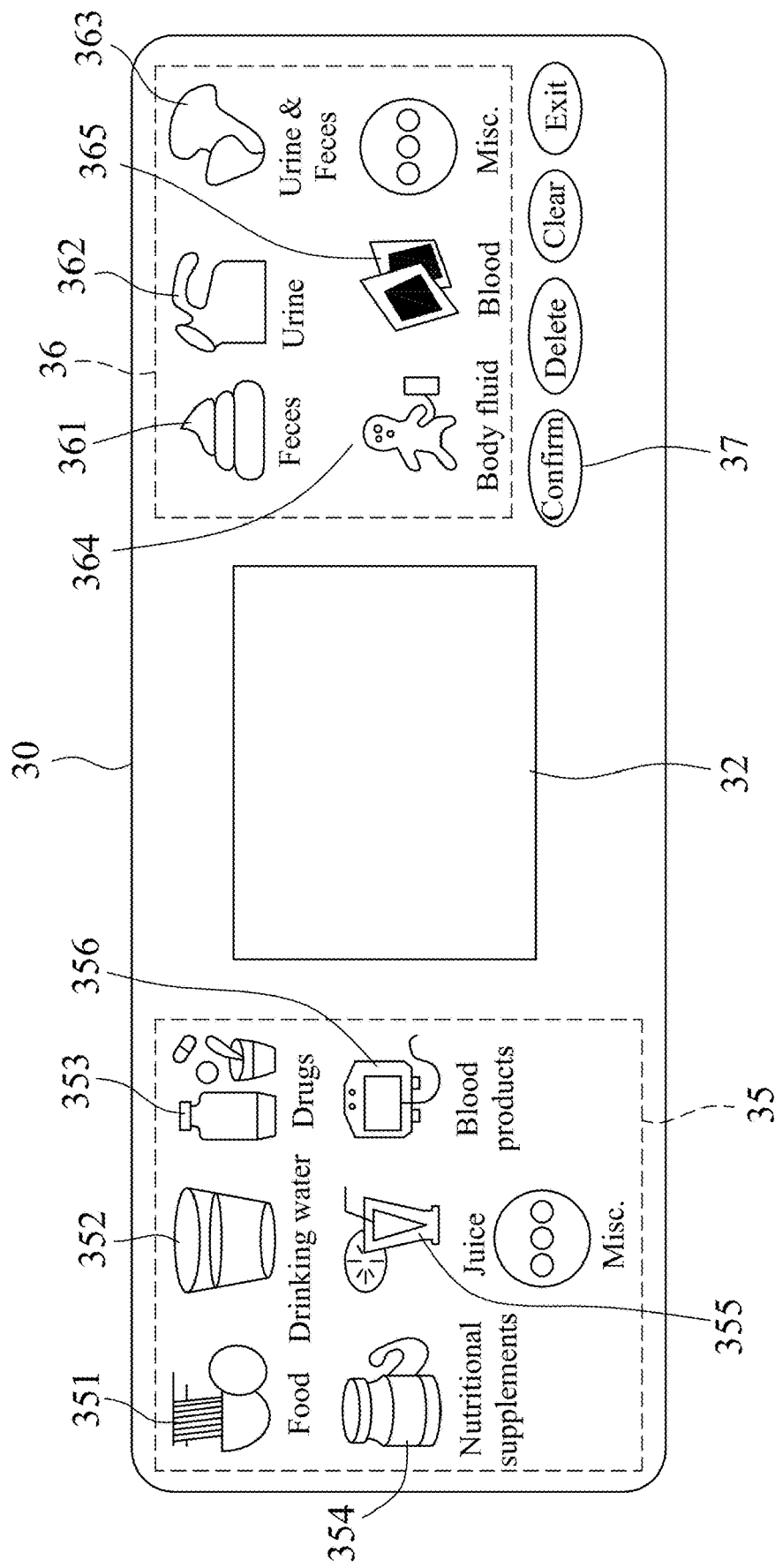
FIG. 4 is a schematic diagram illustrating an example of an operation panel of the weight scale of the weighing system according to the embodiment of the disclosure.

The weight scale 3 includes a scale pan 301 (see FIG. 3). The weight scale 3 is configured to support an object disposed on the scale pan 301, to measure weight of the object, and to output an entry of weight data indicating the weight of the object currently measured. The object may be an empty container, a container having intake substances (e.g., food, drinking water, drugs, nutritional supplements, juice, blood products or the like) to be taken in by the subject, a new absorbent material (e.g., a diaper), a used absorbent material absorbed with output substances (e.g., feces, urine, body fluid, blood or the like) excreted by the subject, an empty receptacle (e.g., a urinal bottle), or a receptacle containing output substances, but is not limited thereto.

The mode switch 31, the display 32, the intake-type button set 35, the output-type button set 36 and the confirmation button 37 are disposed on the weight scale 3, and are electrically connected to the processor 34. Specifically, the weight scale 3 has an operation panel 30 (see FIGS. 3 and 4) and a back side (see FIG. 5) that are opposite to each other. The mode switch 31 is disposed at the back side of the weight scale 3. The display 32, the intake-type button set 35, the output-type button set 36 and the confirmation button 37 are disposed on the operation panel 30 of the weight scale 3. In one embodiment, as shown in FIGS. 4 and 6 to 12, the output-type button set 36 and the intake-type button set 35 are spaced apart from each other in a horizontal direction of the weight scale 3, and the display 32 is disposed between the output-type button set 36 and the intake-type button set 35. In one embodiment, the output-type button set 36 and the intake-type button set 35 are spaced apart from each other in a vertical direction of said weight scale 3 (see FIG. 13).

The intake-type button set 35 includes a plurality of intake-type buttons respectively corresponding to a plurality of intake-type visual symbols that are respectively related to multiple types of intake substances. For example, the intake-type buttons at least include a first intake-type button 351 corresponding to an intake-type visual symbol that is related to food, a second intake-type button 352 corresponding to an intake-type visual symbol that is related to drinking water, a third intake-type 353 corresponding to an intake-type visual symbol that is related to drugs, a fourth intake-type button 354 corresponding to an intake-type visual symbol that is related to nutritional supplements, a fifth intake-type button 355 corresponding to an intake-type visual symbol that is related to juice, and a sixth intake-type button 356 corresponding to an intake-type visual symbol that is related to blood products.

The output-type button set 36 includes a plurality of output-type buttons respectively corresponding to a plurality of output-type visual symbols that are respectively related to multiple types of output substances. For example, the output-type buttons at least include a first output-type button 361 corresponding to an output-type visual symbol that is related to feces, a second output-type button 362 corresponding to an output-type visual symbol that is related to urine, a third output-type button 363 corresponding to an output-type visual symbol that is related to both feces and urine, a fourth output-type button 364 corresponding to an output-type visual symbol that is related to body fluid, and a fifth output-type button 365 corresponding to an output-type visual symbol that is related to blood.

It is worth to note that each of the intake-type visual symbols and the output-type visual symbols may have a form of a graphic, a text or a combination thereof. For example, referring to FIG. 8, the display 32 displays a graphic 323 of a cup containing drinking water as the intake-type visual symbol that is related to drinking water. In some embodiments, the display 32 displays a text "drinking water" as the intake-type visual symbol that is related to drinking water.

Separating the output-type button set 36 from the intake-type button set 35 makes a clear distinction between positions respectively of the output-type buttons and positions respectively of the intake-type buttons, making the buttons easy to identify. Thus, convenience of operation may be ensured and operational mistakes may be prevented.

The display 32 may be a liquid-crystal display (LCD), a light-emitting diode (LED) display, a plasma display panel, a projection display or the like. However, implementation of the display 32 is not limited to the disclosure herein and may vary in other embodiments.

The processor 34, the memory device 33 and the server-communicating unit 382 are disposed in the weight scale 3. The memory device 33, the reader-communicating unit 381 and the server-communicating unit 382 are electrically connected to the processor 34. The reader-communicating unit 381 is configured to be electrically connected to the reader 2 for receiving the identification number of the subject from the reader 2 and to send the identification number of the subject to the processor 34.

Figure 5:
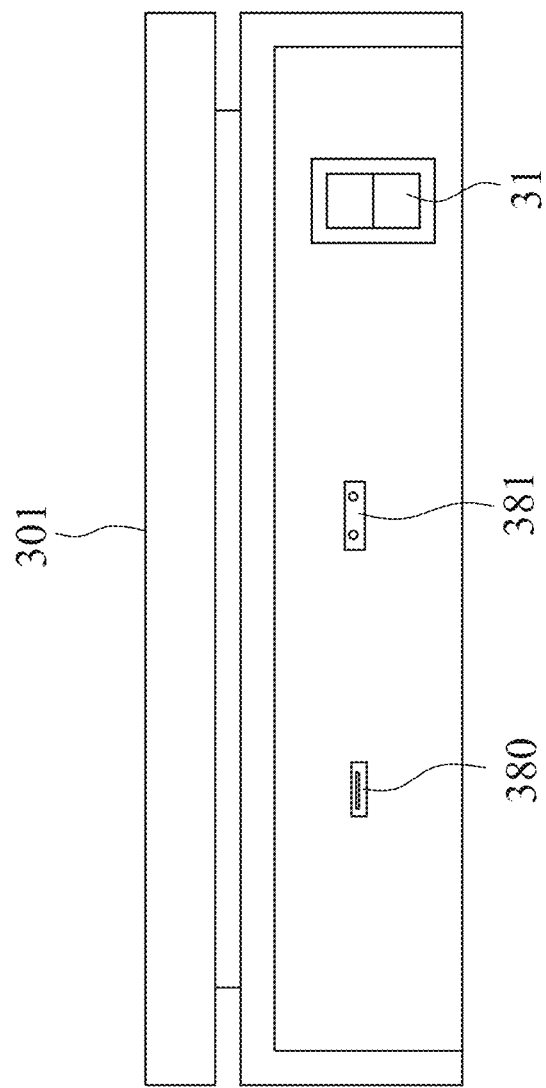
FIG. 5 is a schematic back view of the weight scale of the weighing system according to the embodiment of the disclosure.
Figure 6:
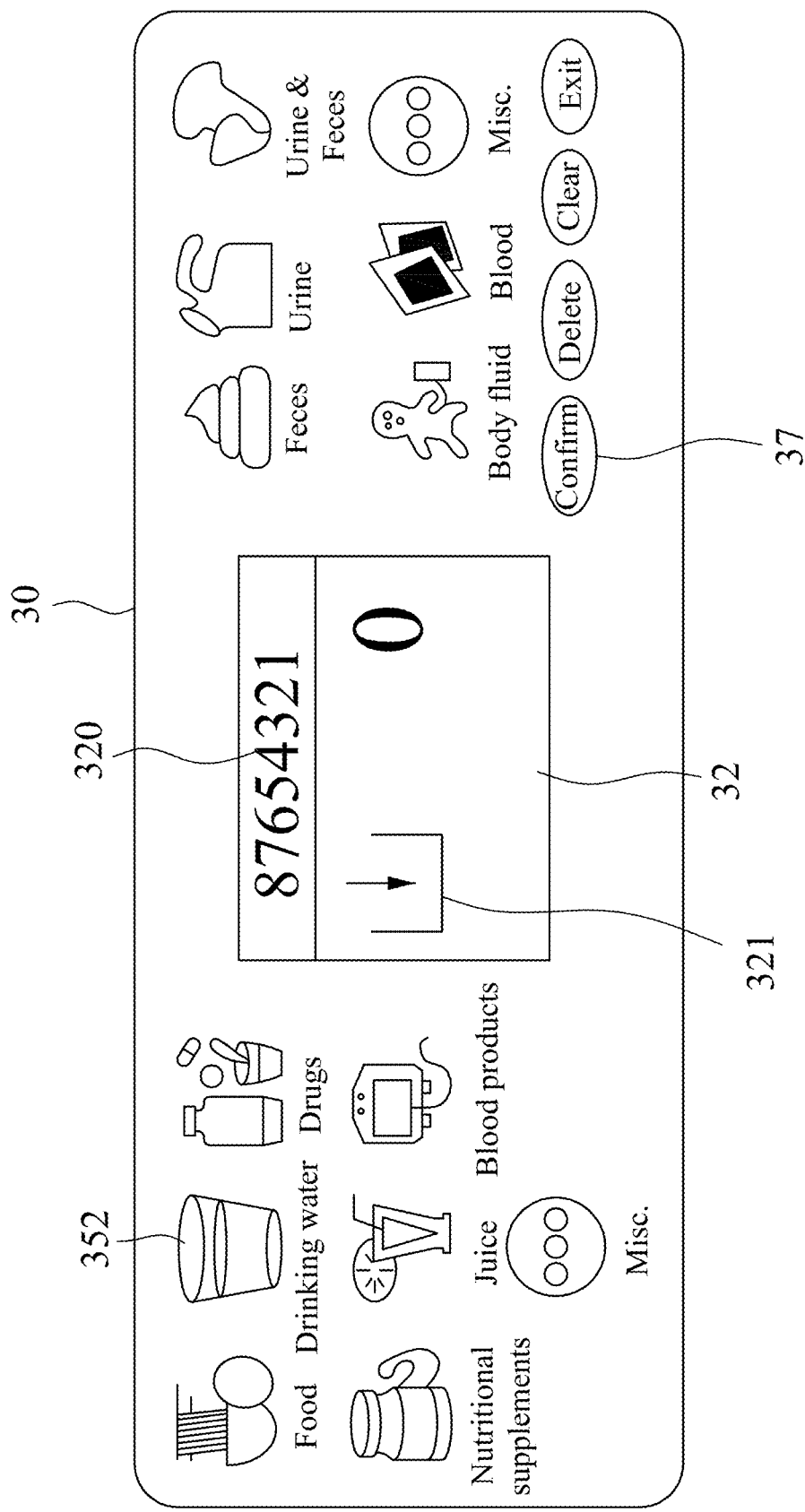
FIG. 6 is a schematic diagram illustrating an example of the operation panel of the weighing system under an intake mode according to the embodiment of the disclosure.

In this embodiment, the reader-communicating unit 381 and the reader 2 are in a wired connection, and the reader-communicating unit 381 is implemented by a universal serial bus (USB) interface disposed at the back side of the weight scale 3 (see FIG. 5). In this way, data transmission between the processor 34 and the reader 2 may be stable and fast, and compatibility issues between the processor 34 and the reader 2 may be avoided. In some embodiments, the reader-communicating unit 381 and the reader 2 are in a wireless connection, and the reader-communicating unit 381 is implemented by a wireless communication module that is disposed in the weight scale 3 and that supports wireless communication standards, such as Bluetooth® technology standards, Wi-Fi technology standards, and/or the like.

In this embodiment, the server-communicating unit 382 is configured to be wirelessly connected to the computing server 4. In particular, the server-communicating unit 382 is implemented to be a network interface controller or a wireless transceiver that supports wireless communication standards, such as Bluetooth® technology standards, Wi-Fi technology standards and/or cellular network technology standards, but is not limited thereto. In some embodiments, the server-communicating unit 382 may include a mobile communication module supporting telecommunication using Long-Term Evolution (LTE), the third generation (3G) and/or fifth generation (5G) of wireless mobile telecommunications technology, and/or the like, but is not limited thereto. In this way, the computing server 4 can be distal from the weight scale 3, the reader 2 and the mobile cart 1. For example, the computing server 4 may be located in one room while the assembly of the weight scale 3, the reader 2 and the mobile cart 1 is located in a different room. Consequently, flexibility of using the weighing system according to the disclosure may be enhanced.

The memory device 33 may be implemented by random access memory (RAM), double data rate synchronous dynamic random access memory (DDR SDRAM), read only memory (ROM), programmable ROM (PROM), flash memory, a hard disk drive (HDD), a solid state disk (SSD), electrically-erasable programmable read-only memory (EEPROM) or any other volatile/non-volatile memory devices, but is not limited thereto.

The processor 34 may be implemented by a central processing unit (CPU), a microprocessor, a micro control unit (MCU), a system on a chip (SoC), or any circuit configurable/programmable in a software manner and/or hardware manner to implement functionalities discussed in this disclosure.

The processor 34 is configured to receive the identification number of the subject from the reader 2, and to control the display 32 to display the identification number of the subject (e.g., the patient number 320 "87654321" shown in FIG. 6). In some embodiments, the processor 34 may obtain the identification number of the subject based on a user input (e.g., the user input may be generated by using a keyboard electrically connected to the processor 34), and the reader 2 may be omitted. The processor 34 is further configured to operate in one of an intake mode and an output mode, and to receive the entry of weight data from the weight scale 3. The mode switch 31 is, for example, a toggle switch, and is configured to be operated to enable the processor 34 to operate in one of the intake mode and the output mode. It is worth to note that the processor 34 would create, based on the identification number of the subject, a subject-specific file folder exclusively for the subject in the memory device 33, and store data (e.g., a value of weight obtained from the entry of weight data) related to the subject in the subject-specific file folder when operating in the intake mode or in the output mode.

When operating in the intake mode, the processor 34 is configured to implement the following operations. First, the processor 34 controls the display 32 to display an intake-mode symbol 321 as shown in FIG. 6, and to determine whether any one of the intake-type buttons and the output-type buttons is pressed. Seeing the intake-mode symbol 321 on the display 32, a medical professional (e.g., a nurse) would be assured that the processor 34 is operating in the intake mode. In the intake mode, the processor 34 is non-responsive to the output-type buttons in the sense that the processor 34 does not control the display 32 to display any one of the output-type visual symbols when it is determined that one of the output-type buttons is pressed, and does not take any follow-up action even if the processor 34 subsequently receives an entry of weight data from the weight scale 3, so operational mistakes may be prevented. When it is determined that one of the intake-type buttons is pressed (hereinafter referred to as "pressed intake-type button"), the processor 34 controls the display 32 to display one of the intake-type visual symbols that corresponds to the pressed intake-type button. Later, in response to receipt of an entry of weight data from the weight scale 3, the processor 34 obtains a first value of intake-related weight (i.e., a value of pre-intake weight) based on the entry of weight data, controls the display 32 to display the value of pre-intake weight, and stores the value of pre-intake weight in the memory device 33 (more specifically, in the subject-specific file folder). It should be noted that when storing the value of pre-intake weight in the memory device 33, at the same time, the processor 34 also stores in the memory device 33 (more specifically, in the subject-specific file folder) an intake-type correspondence indicator that associates the value of pre-intake weight with one of the types of intake substances that is related to the one of the intake-type visual symbols which corresponds to the pressed intake-type button. By virtue of storing the value of pre-intake weight and the intake-type correspondence indicator in the subject-specific file folder, the value of pre-intake weight and the intake-type correspondence indicator are associated with the identification number corresponding to the subject-specific file folder.

Subsequently, when operating in the intake mode and receiving the identification number of the subject from the reader 2 again, based on the intake-type correspondence indicator stored in the memory device 33, the processor 34 is configured to control the display 32 to display one of the intake-type visual symbols that is related to the value of pre-intake weight stored in the memory device 33, and to determine whether one of the intake-type buttons that corresponds to said one of the intake-type visual symbols (i.e., the pressed intake-type button) is pressed again. When it is determined that the pressed intake-type button is pressed again, the processor 34 is configured to control the display 32 to further display the value of pre-intake weight stored in the memory device 33. In response to receipt of another entry of weight data from the weight scale 3, the processor 34 is configured to obtain a second value of intake-related weight (i.e., a value of post-intake weight) based on said another entry of weight data, to control the display 32 to further display the value of post-intake weight, to calculate a difference between the value of pre-intake weight and the value of post-intake weight as a value of intake weight, and to output the value of intake weight, for example, to the computing server 4.

Figure 7:
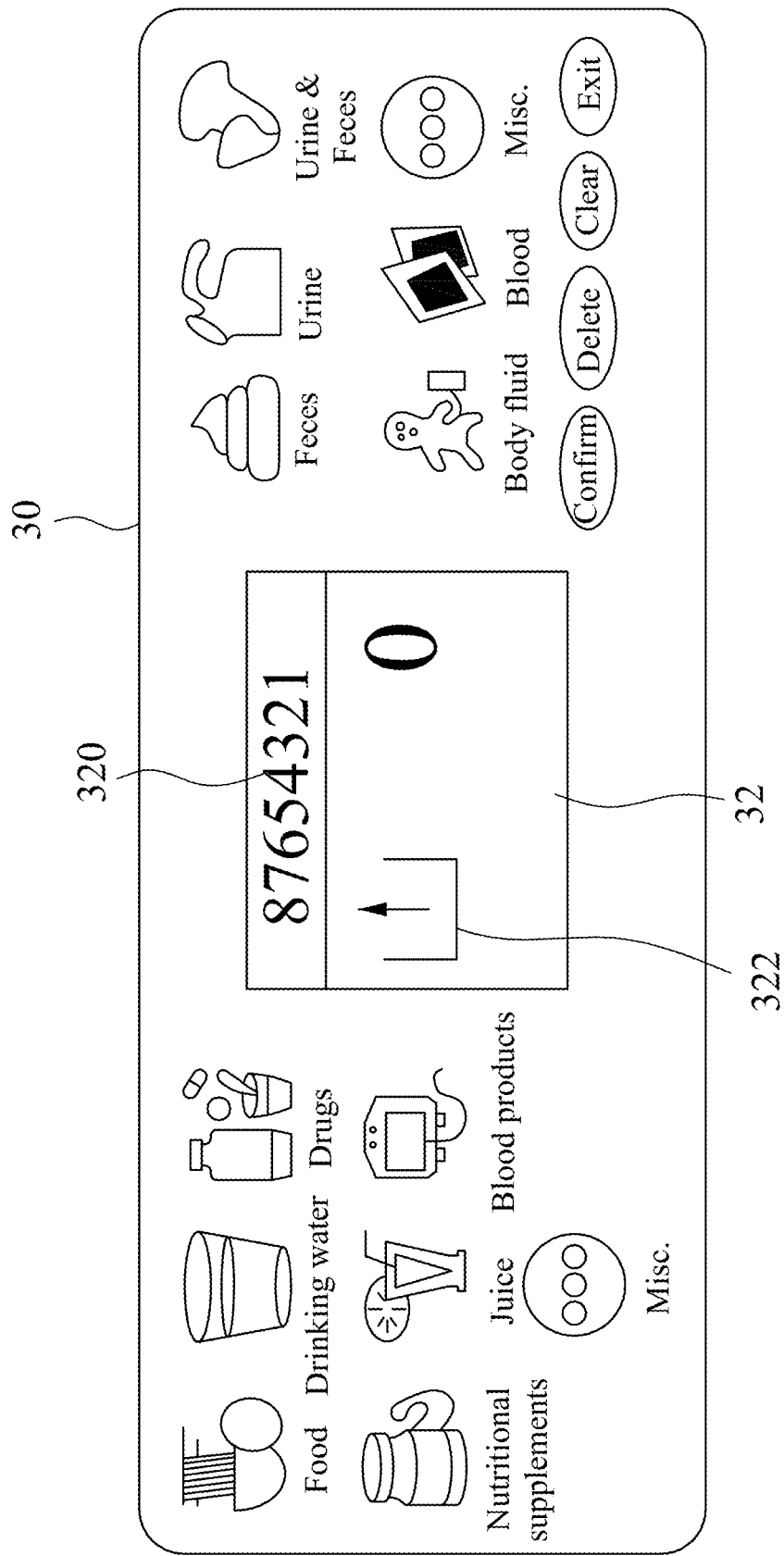
FIG. 7 is a schematic diagram illustrating an example of the operation panel of the weighing system under an output mode according to the embodiment of the disclosure.
Figure 8:
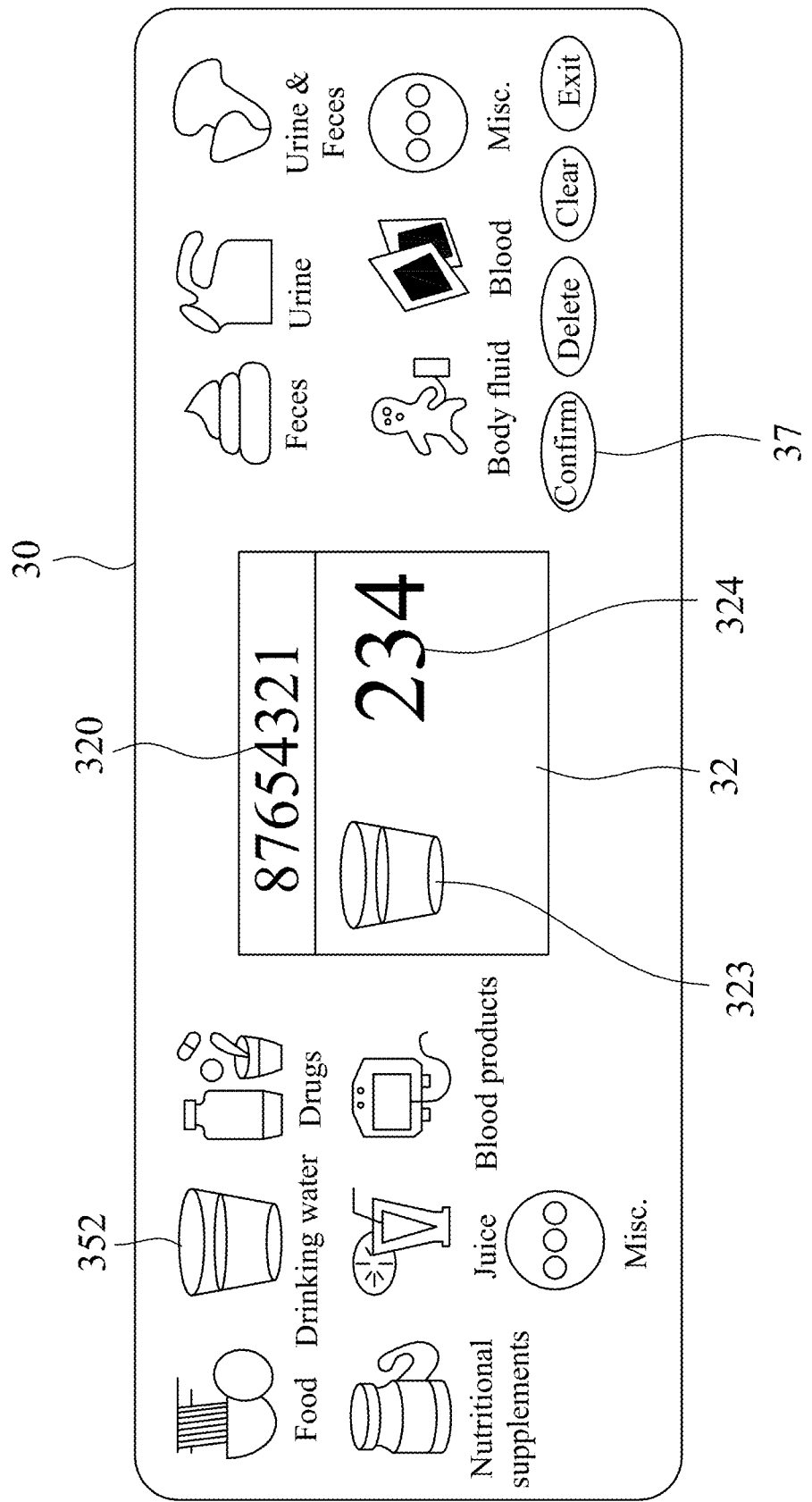
FIGS. 8 to 12 are schematic diagrams illustrating an example of operating the weighing system under the intake mode according to the embodiment of the disclosure.

When operating in the output mode, the processor 34 is configured to implement the following operations. First, the processor 34 controls the display 32 to display an output-mode symbol 322 as shown in FIG. 7, and determines whether any one of the intake-type buttons and the output-type buttons is pressed. Seeing the output-mode symbol 322 on the display 32, the medical professional would be assured that the processor 34 is operating in the output mode. In the output mode, the processor 34 is non-responsive to the intake-type buttons in the sense that the processor 34 does not control the display 32 to display any one of the intake-type visual symbols when it is determined that one of the intake-type buttons is pressed, and does not take any follow-up action even if the processor 34 subsequently receives an entry of weight data from the weight scale 3, so operational mistakes may be prevented. When it is determined that one of the output-type buttons is pressed (hereinafter referred to as "pressed output-type button"), the processor 34 controls the display 32 to display one of the output-type visual symbols that corresponds to the pressed output-type button. Later, in response to receipt of an entry of weight data from the weight scale 3, the processor 34 obtains a first value of output-related weight (i.e., a value of post-output weight) based on the entry of weight data, controls the display 32 to display the value of post-output weight, and stores the value of post-output weight in the memory device 33 (more specifically, in the subject-specific file folder). It should be noted that when storing the value of post-output weight in the memory device 33, at the same time, the processor 34 also stores in the memory device 33 (more specifically, in the subject-specific file folder) an output-type correspondence indicator that associates the value of post-output weight with one of the types of output substances that is related to the one of the output-type visual symbols which corresponds to the pressed output-type button. By virtue of storing the value of post-output weight and the output-type correspondence indicator in the subject-specific file folder, the value of post-output weight and the output-type correspondence indicator are associated with the subject whose identification number corresponds to the subject-specific file folder.

Subsequently, when operating in the output mode and receiving the identification number of the subject from the reader 2 again, based on the output-type correspondence indicator stored in the memory device 33, the processor 34 is configured to control the display 32 to display one of the output-type visual symbols that is related to the value of post-output weight stored in the memory device 33, and to determine whether one of the output-type buttons that corresponds to said one of the output-type visual symbols (i.e., the pressed output-type button) is pressed again. When it is determined that the pressed output-type button is pressed again, the processor 34 is configured to control the display 32 to further display the value of post-output weight stored in the memory device 33. In response to receipt of another entry of weight data from the weight scale 3, the processor 34 is configured to obtain a second value of output-related weight (i.e., a value of pre-output weight) based on said another entry of weight data, to control the display 32 to further display the value of pre-output weight, to calculate a difference between the value of pre-output weight and the value of post-output weight as a value of output weight, and to output the value of output weight, for example, to the computing server 4. In some embodiments, the second value of output-related weight is obtained based on a user input to the weight scale 3 (e.g., the user input may be generated by using a keyboard electrically connected to the weight scale 3).

Figure 12:
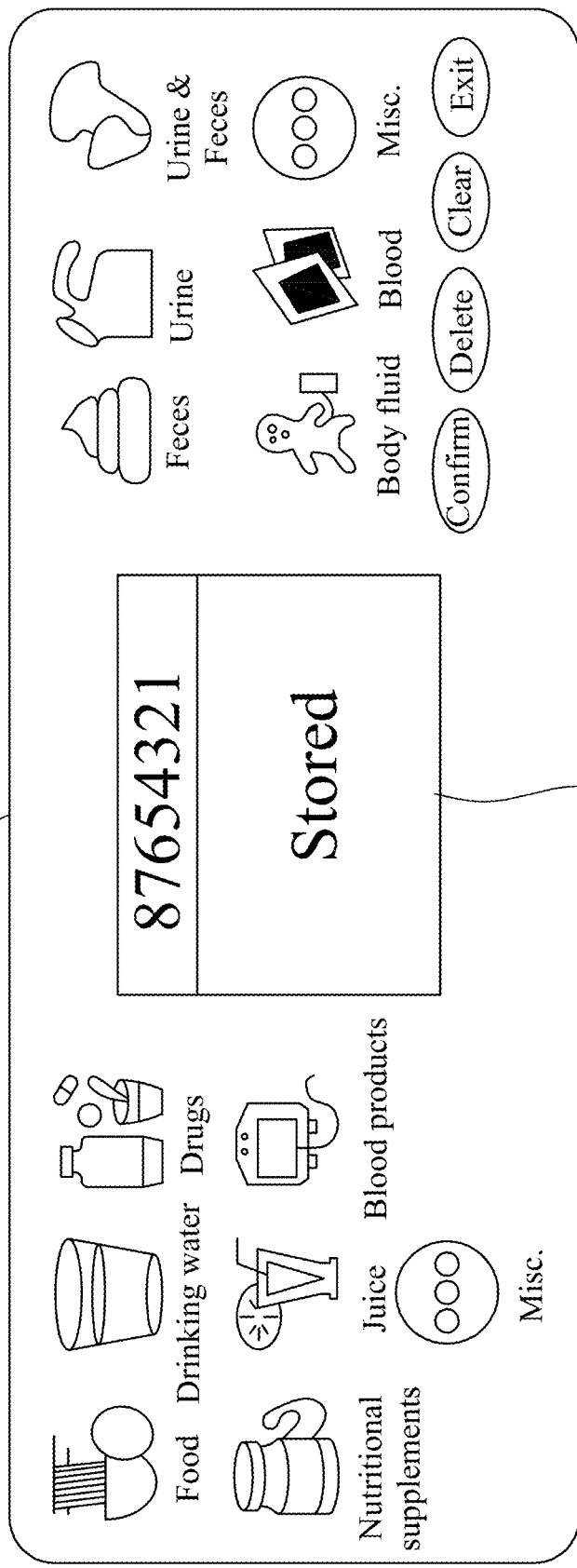
Figure 13:
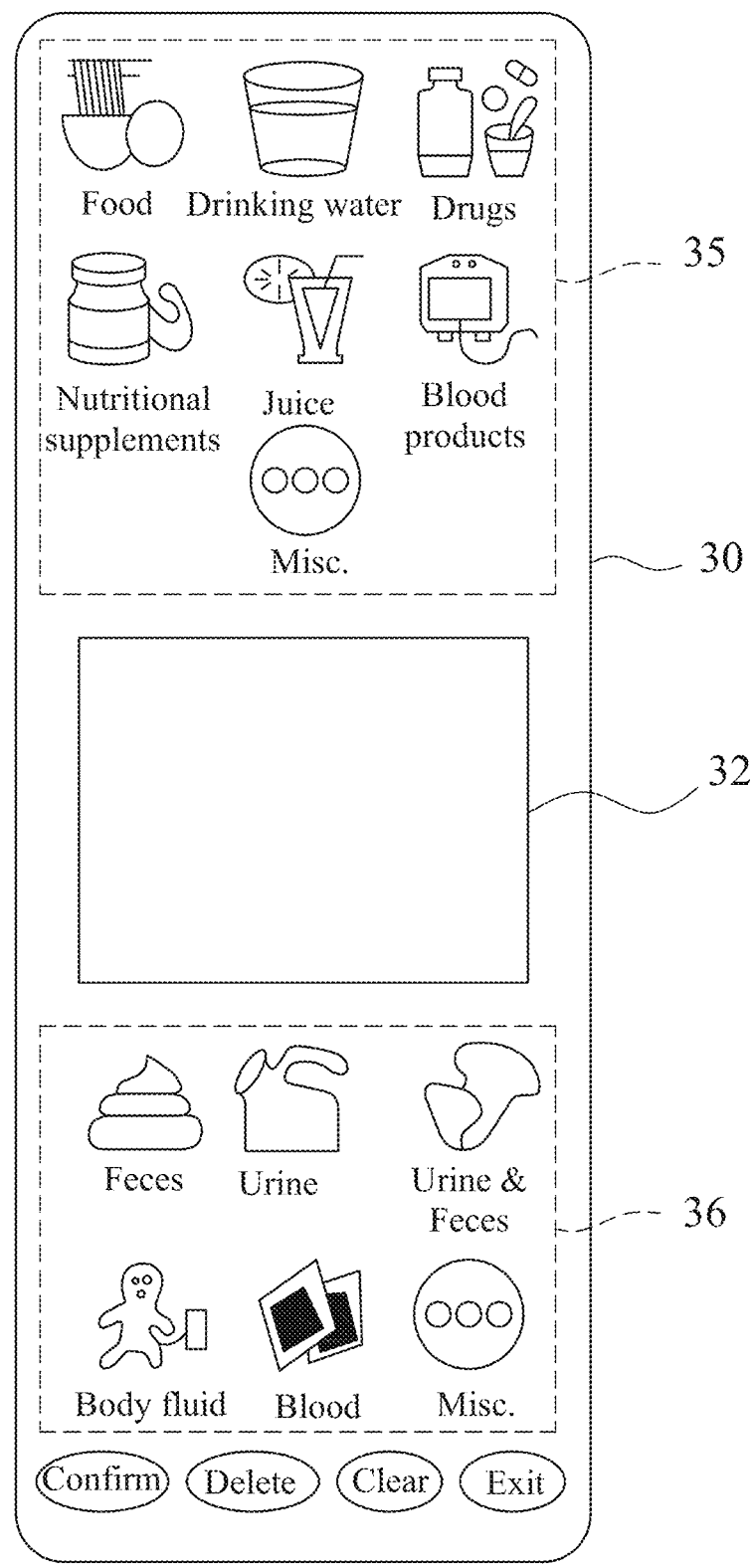
FIG. 13 is a schematic diagram illustrating another example of the operation panel of the weight scale of the weighing system according to the embodiment of the disclosure.

To facilitate understanding, an example of operating the weighing system is described as follows with reference to FIGS. 6 and 8 to 12. At the beginning, a medical professional uses the reader 2 (see FIG. 3) to read the identifier disposed on a wristband (not shown) worn by a subject (not shown) to obtain the identification number of the subject, and the processor 34 (see FIG. 2) controls the display 32 to display the identification number (i.e., the patient number 320 "87654321" shown in FIG. 6) when receiving the identification number from the reader 2. To obtain a value of intake weight of drinking water consumed by the subject, the medical professional operates the mode switch 31 (see FIG. 5) to make the processor 34 operate in the intake mode, and the processor 34 controls the display 32 to display the intake-mode symbol 321 (see FIG. 6). Then, the medical professional presses the second intake-type button 352 corresponding to the intake-type visual symbol that is related to drinking water, and the processor 34 controls the display 32 to display the intake-type visual symbol that is related to drinking water (i.e., the graphic 323 showing a cup containing drinking water in FIG. 8) so as to notify the medical professional that the value of pre-intake weight for drinking water is to be determined. Next, the medical professional puts a container that contains drinking water on the scale pan 301 of the weight scale 3 (see FIG. 3). The weight scale 3 measures the weight of the container that contains drinking water, and outputs an entry of weight data to the processor 34. The processor 34 obtains the value of pre-intake weight based on the entry of weight data, and controls the display 32 to displays a number 324 representing the value of pre-intake weight (e.g., "234" shown in FIG. 8, which means that the value of pre-intake weight is 234 g). Thereafter, the medical professional presses the confirmation button 37 to make the processor 34 store the value of pre-intake weight in the memory device 33 (see FIG. 2), and the processor 34 controls the display 32 to display a message indicating that the value of pre-intake weight has been stored as shown in FIG. 12.

Figure 9:
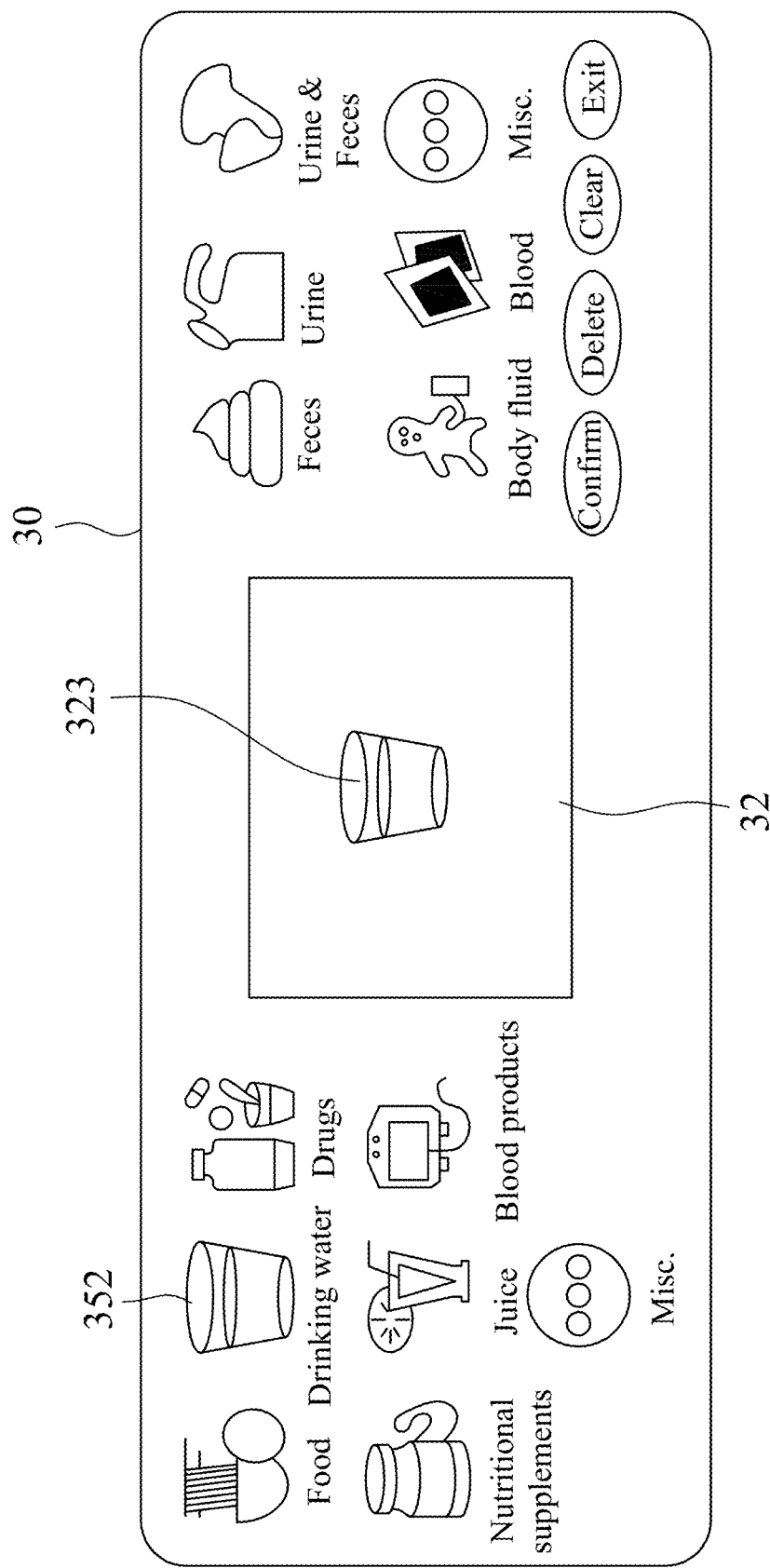
Figure 10:
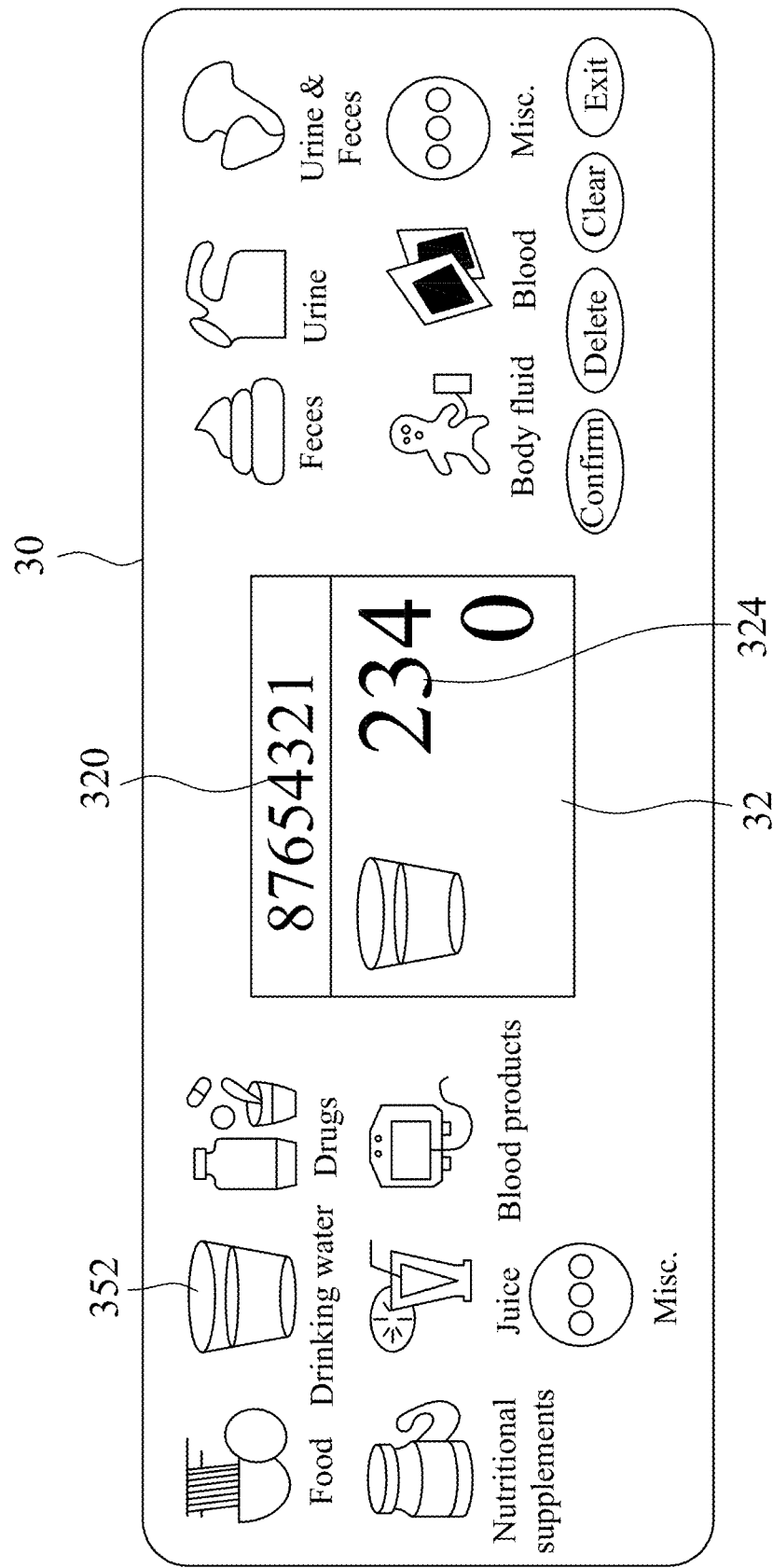
Figure 11:
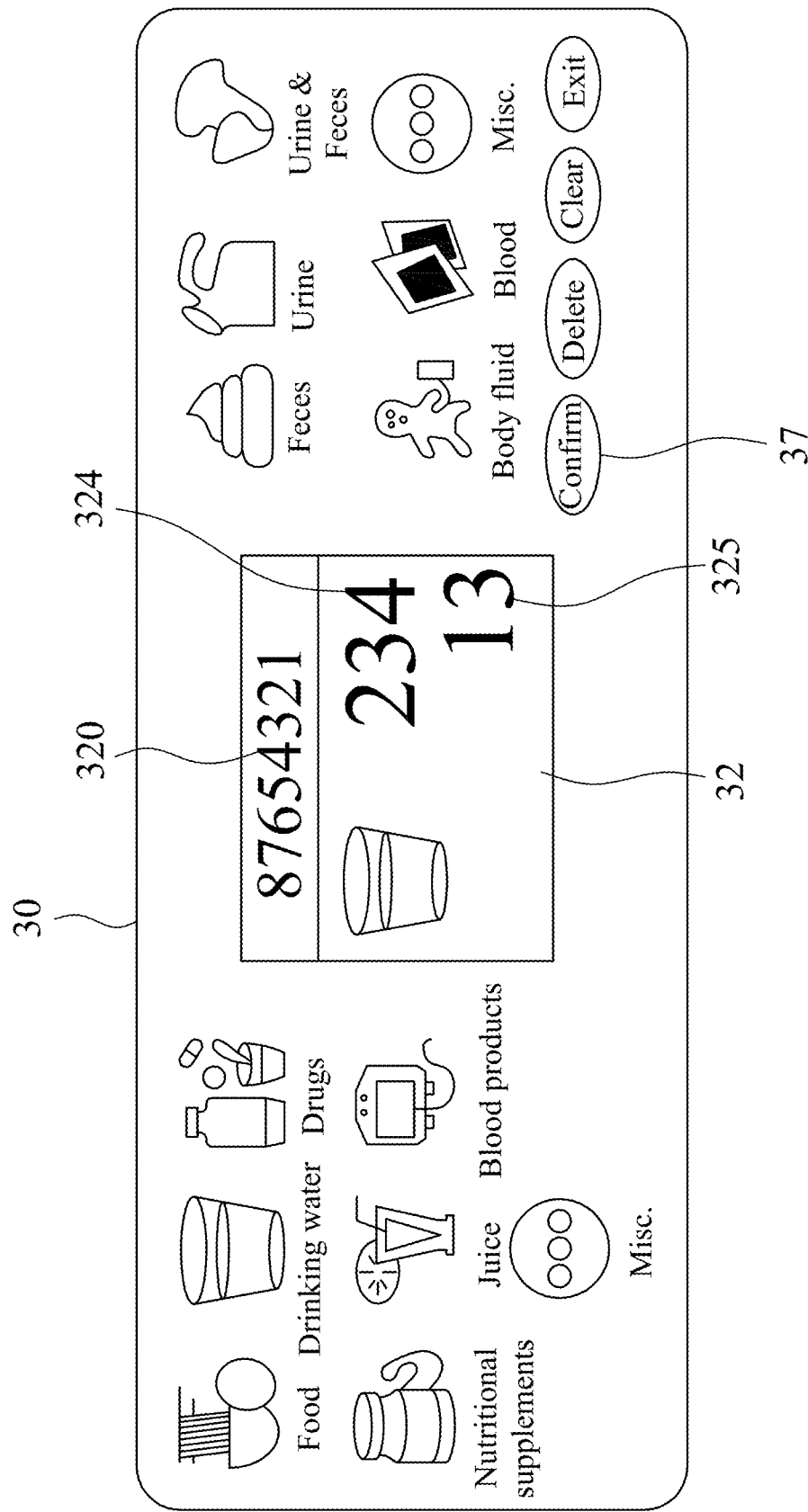

After the subject has consumed some of the drinking water from the container, the medical professional ensures that the processor 34 is operating in the intake mode by operating the mode switch 31. Then, the medical professional again uses the reader 2 to read the identifier to obtain the identification number of the subject, and the processor 34 operating in the intake mode controls the display 32 to display the identification number of the subject when receiving the identification number from the reader 2. At the same time, as shown in FIG. 9, the processor 34 controls the display 32 to display the intake-type visual symbol that is related to drinking water so as to notify the medical professional that the value of pre-intake weight for the container that contains drinking water has been obtained by the weighing system. After the medical professional presses the second intake-type button 352, the processor 34 controls the display 32 to display the number 324 representing the value of pre-intake weight (i.e., "234" shown in FIG. 10) stored in the memory device 33 and a number 325 representing the value of post-intake weight (i.e., "0" shown in FIG. 10, which means that the value of post-intake weight is yet to be determined). Next, the medical professional puts the container, from which the subject has consumed some water, on the scale pan 301 of the weight scale 3. The weight scale 3 measures the weight of the container, and outputs another entry of weight data to the processor 34. The processor 34 obtains the value of post-intake weight based on the another entry of weight data, and controls the display 32 to renew the number 325 representing the value of post-intake weight (e.g., "13" shown in FIG. 11, which means that the value of post-intake weight is 13 g). Thereafter, the medical professional presses the confirmation button 37 to make the processor 34 calculate a difference between the value of pre-intake weight and the value of post-intake weight as the value of intake weight (i.e., 234 g−13 g=221 g), which represents an amount of drinking water consumed by the subject.

Similarly, to obtain a value of output weight of urine excreted by the subject, the medical professional operates the mode switch 31 to make the processor 34 operate in the output mode, and the processor 34 controls the display 32 to display the output-mode symbol 322 (see FIG. 7). Then, the medical professional presses the second output-type button 362 (see FIG. 4) corresponding to the output-type visual symbol that is related to urine, and the processor 34 controls the display 32 to display the output-type visual symbol that is related to urine so as to notify the medical professional that the value of post-output weight for urine is to be determined. Next, the medical professional puts a used diaper (i.e., the diaper has absorbed urine of the subject) on the scale pan 301 of the weight scale 3. The weight scale 3 measures the weight of the used diaper, and outputs an entry of weight data to the processor 34. The processor 34 obtains the value of post-output weight (i.e., the weight of the used diaper) based on the entry of weight data, and controls the display 32 to displays a number representing the value of pre-output weight. Thereafter, the medical professional presses the confirmation button 37 to make the processor 34 store the value of post-output weight in the memory device 33, and the processor 34 controls the display 32 to display a message indicating that the value of post-output weight has been stored as shown in FIG. 12. When the medical professional again presses the second output-type button 362, the processor 34 operating in the output mode controls the display 32 to display the number representing the value of post-output weight stored in the memory device 33. Next, the medical professional puts a new diaper on the scale pan 301 of the weight scale 3. The weight scale 3 measures the weight of the new diaper, and outputs another entry of weight data to the processor 34. The processor 34 obtains the value of pre-output weight (i.e., the weight of the new diaper) based on said another entry of weight data, and controls the display 32 to display a number representing the value of pre-output weight. Thereafter, the medical professional presses the confirmation button 37 to make the processor 34 calculate a difference between the value of pre-output weight and the value of post-output weight as the value of output weight, which represents an amount of urine excreted by the subject.

The processor 34 is further configured to send the value of intake weight and the value of output weight via the server-communicating unit 382 to the computing server 4 for storage. The medical professional is able to utilize the computing server 4 to read a nursing record that is related to intake and output (I&O) of the subject, e.g., to read the nursing record by a browser installed in the computing server 4. The nursing record may contain a plot depicting a trend of values of intake weight for each intake substance and a trend of values of output weight for each output substance (i.e., the values of intake weight and the values of output weight recorded at different time points), and the medical professional would be able to take an appropriate action based on his/her observation of these trends.

Thereafter, the computing server 4 is configured to determine which of the value of intake weight and the value of output weight is greater, to calculate an absolute value of a difference between the value of intake weight and the value of output weight as an intake-output difference, and to determine whether the intake-output difference is greater than a threshold value. It should be noted that only the value of intake weight and the value of output weight that are predetermined to be relevant (i.e., the intake substance and the output substance to which the value of intake weight and the value of output weight respectively correspond are relevant, e.g., drinking water and urine) will be taken into account when calculating the intake-output difference. The computing server 4 is configured to output a first alert corresponding to a relationship between the value of intake weight and the value of output weight when it is determined that the intake-output difference is greater than the threshold value. Notified by the first alert, medical professionals may be able to take an appropriate action in time.

It is worth to note that the first alert can at least indicate a condition that the value of intake weight is greater than the value of output weight, or a condition that the value of output weight is greater than the value of intake weight.

In one embodiment, the computing server 4 is further configured to calculate a sum of a plurality of values of intake weight that are received from the processor 34 within a preset time period (e.g., eight hours or twenty-four hours) as a value of accumulated intake weight, to calculate a sum of a plurality of values of output weight that are received from the processor 34 within the preset time period as a value of accumulated output weight, to determine which of the value of accumulated intake weight and the value of accumulated output weight is greater, to calculate an absolute value of a difference between the value of accumulated intake weight and the value of accumulated output weight as the intake-output difference, to determine whether the intake-output difference is greater than the threshold value, and to output a second alert corresponding to a relationship between the value of accumulated intake weight and the value of accumulated output weight when it is determined that the intake-output difference is greater than the threshold value. Notified by the second alert, medical professionals may be able to take an appropriate action in time.

It is worth to note that the second alert can at least indicate a condition that the value of accumulated intake weight is greater than the value of accumulated output weight, or a condition that the value of accumulated output weight is greater than the value of accumulated intake weight.

For example, in a scenario where the preset time period is twenty-four hours, the threshold value is 1000 g, the value of accumulated intake weight related to drinking water is 2000 g and the value of accumulated output weight related to urine is 500 g, the computing server 4 would calculate the intake-output difference as 1500 g (i.e., |2000 g−500 g|=1500 g), determine that the intake-output difference is greater than the threshold value (i.e., 1000 g) and that the value of accumulated intake weight is greater than the value of accumulated output weight, and output the second alert to advise a medical professional to treat the subject with diuretics. In another scenario where the preset time period is twenty-four hours, the threshold value is 1000 g, the value of accumulated intake weight related to drinking water is 500 g and the value of accumulated output weight related to urine is 2000 g, the computing server 4 would calculate the intake-output difference as 1500 g (i.e., |500 g−2000 g|=1500 g), determine that the intake-output difference is greater than the threshold value (i.e., 1000 g) and that the value of accumulated intake weight is less than the value of accumulated output weight, and output the second alert to advise a medical professional to supply the subject with water.

In some embodiments, the processor 34 may be configured to store the value of intake weight and the value of output weight, to calculate the intake-output difference based on the value of intake weight and the value of output weight, to determine whether the intake-output difference is greater than the threshold value, and to output the first alert when it is determined that the intake-output difference is greater than the threshold value.

In one embodiment, the computing server 4 is configured to obtain, via network communication, a preset value from an external device (e.g., a personal computer, a smartphone or the like) as the threshold value, where the preset value is determined by a medical professional (e.g., a doctor) based on practical needs and his/her experience and expertise, and the medical professional operates the external device to store the preset value.

In one embodiment, the computing server 4 is configured to allow a user to input the threshold value (e.g., by using a keyboard of the computing server 4).

In one embodiment, the computing server 4 is configured to implement an artificial intelligence (AI) algorithm for predicting occurrence of acute kidney injury (AKI) based on input parameters that are related to age, gender, drug usage, physiological values (e.g., heart rate, blood pressure, or the like), AKI-related disease condition (e.g., whether or not the subject is diagnosed with diabetes, hypertension, cardiovascular diseases, chronic hepatitis, chronic obstructive pulmonary disease, or the like), and results of hematology tests on blood urea nitrogen, creatinine or the like. When it is predicted that AKI has occurred, the computing server 4 outputs a notification.

It is worth to note that in one embodiment, when the processor 34 operates in the intake mode, the value of post-intake weight (e.g., the weight of a container emptied by the subject) is obtained prior to the value of pre-intake weight (e.g., the weight of a container containing the same amount of water as the one given to the subject for consumption); that is to say, the first value of intake-related weight is the value of post-intake weight, and the second value of intake-related weight is the value of pre-intake weight. In one embodiment, when the processor 34 operates in the output mode, the value of pre-output weight (e.g., the weight of a new diaper) is obtained prior to the value of post-output weight (e.g., the weight of a used diaper); that is to say, the first value of output-related weight is the value of pre-output weight, and the second value of output-related weight is the value of post-output weight.

In one embodiment, the computing server 4 is further configured to output a third alert when it is determined that the value of output weight which corresponds to blood is greater than a blood-loss threshold value. The third alert indicates that the subject may be experiencing severe blood loss. Notified by the third alert, medical professionals may be able to perform further examinations about internal bleeding (also called internal hemorrhage) and/or a blood transfusion to the subject in time.

In one embodiment, the computing server 4 is further configured to output a fourth alert when it is determined that the value of output weight which corresponds to body fluid is greater than a body-fluid-deprivation threshold value. The fourth alert indicates that the subject may be experiencing body-fluid deprivation. Notified by the fourth alert, medical professionals may be able to administer fluid to the subject via an intravenous therapy (IV) drip in time.

To sum up, for the weighing system according to the disclosure, when operating in the intake mode and receiving an identification number of a subject from the reader 2, the processor 34 controls the display 32 to display one of the intake-type visual symbols corresponding to one of the intake-type buttons that is determined to be pressed by the user, and in response to receipt of an entry of weight data from the weight scale 3, controls the display 32 to display a value of pre-intake weight obtained based on the entry of weight data, and stores the value of pre-intake weight in the memory device 33. Moreover, when operating in the intake mode and receiving the identification number of the subject from the reader 2 again, the processor 34 controls the display 32 to display one of the intake-type visual symbols that is related to the value of pre-intake weight stored in the memory device 33, controls the display 32 to further display the value of pre-intake weight stored in the memory device 33 when it is determined that the one of the intake-type buttons is pressed again, and in response to receipt of another entry of weight data from the weight scale 3, controls the display 32 to further display a value of post-intake weight, calculates a difference between the value of pre-intake weight and the value of post-intake weight as a value of intake weight, and outputs the value of intake weight. In the output mode, the processor 34 performs the operations similar to those in the intake mode. In this way, tasks related to keeping a nursing record may be facilitated.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A weighing system that facilitates keeping a nursing record for a subject, the subject being assigned an identification number that is stored by an identifier, said weighing system comprising:
   a reader configured to read the identifier to obtain the identification number of the subject;
   a weight scale configured to support an object, to measure weight of the object, and to output an entry of weight data indicating the weight of the object currently measured;
   a processor disposed in said weight scale, electrically connected to said reader and said weight scale, and configured to receive the identification number of the subject from said reader, to receive the entry of weight data from said weight scale, and to operate in one of an intake mode and an output mode;
   a mode switch disposed on said weight scale, electrically connected to said processor, and configured to be operated to enable said processor to operate in one of the intake mode and the output mode;
   a display disposed on said weight scale, electrically connected to said processor, and configured to be controlled by said processor to display the identification number of the subject;
   a memory device disposed in said weight scale, and electrically connected to said processor;
   an intake-type button set disposed on said weight scale, electrically connected to said processor, and including a plurality of intake-type buttons that respectively correspond to a plurality of intake-type visual symbols which are respectively related to a plurality of types of intake substances; and
   an output-type button set disposed on said weight scale, spaced apart from said intake-type button set, electrically connected to said processor, and including a plurality of output-type buttons that respectively correspond to a plurality of output-type visual symbols which are respectively related to a plurality of types of output substances,
   wherein said processor is further configured, when operating in the intake mode, to
      determine whether any one of said intake-type buttons and said output-type buttons is pressed,
      when it is determined that one of said intake-type buttons is pressed, control said display to display one of the intake-type visual symbols that corresponds to the one of said intake-type buttons, and then in response to receipt of the entry of weight data from said weight scale, obtain a first value of intake-related weight based on the entry of weight data, control said display to display the first value of intake-related weight, and store the first value of intake-related weight in said memory device, and
      when it is determined that one of said output-type buttons is pressed, not control said display to display any one of the output-type visual symbols,
   wherein said processor is further configured, when operating in the output mode, to
      determine whether any one of said intake-type buttons and said output-type buttons is pressed,
      when it is determined that one of said output-type buttons is pressed, control said display to display one of the output-type visual symbols that corresponds to the one of said output-type buttons, and then in response to receipt of the entry of weight data from said weight scale, obtain a first value of output-related weight based on the entry of weight data, control said display to display the first value of output-related weight, and store the first value of output-related weight in said memory device, and
      when it is determined that one of said intake-type buttons is pressed, not control said display to display any one of the intake-type visual symbols.

2. The weighing system as claimed in claim 1, wherein said processor is further configured, when operating in the intake mode and receiving the identification number of the subject from said reader again, to:
   control said display to display one of the intake-type visual symbols that is related to the first value of intake-related weight stored in said memory device,
   determine whether the one of said intake-type buttons is pressed again, and
   when it is determined that the one of the intake-type buttons is pressed again, control said display to further display the first value of intake-related weight stored in said memory device, and then in response to receipt of another entry of weight data from said weight scale, obtain a second value of intake-related weight based on the another entry of weight data, control said display to further display the second value of intake-related weight, calculate a difference between the first value of intake-related weight and the second value of intake-related weight as a value of intake weight, and output the value of intake weight.

3. The weighing system as claimed in claim 2, wherein said processor is further configured, when operating in the output mode and receiving the identification number of the subject from said reader again, to:
   control said display to display one of the output-type visual symbols that is related to the first value of output-related weight stored in said memory device,
   determine whether the one of said output-type buttons is pressed again, and
   when it is determined that the one of said output-type buttons is pressed again, control said display to further display the first value of output-related weight stored in said memory device, and then in response to receipt of still another entry of weight data from said weight scale, obtain a second value of output-related weight based on the still another entry of weight data, control said display to further display the second value of output-related weight, calculate a difference between the first value of output-related weight and the second value of output-related weight as a value of output weight, and output the value of output weight.

4. The weighing system as claimed in claim 3, further comprising:
   a computing server; and
   a server-communicating unit disposed in said weight scale, electrically connected to said processor, and configured to be wirelessly connected to said computing server,
   wherein said processor is further configured to send the value of intake weight and the value of output weight via said server-communicating unit to said computing server for storage,
   wherein said computing server is configured to calculate an absolute value of a difference between the value of intake weight and the value of output weight as an intake-output difference, to determine whether the intake-output difference is greater than a threshold value, and to output an alert corresponding to a relationship between the value of intake weight and the value of output weight when it is determined that the intake-output difference is greater than the threshold value.

5. The weighing system as claimed in claim 4, wherein said processor is further configured to send the value of intake weight and the value of output weight via said server-communicating unit to said computing server for storage.

6. The weighing system as claimed in claim 4, wherein said computing server is further configured to obtain a preset value from an external device as the threshold value.

7. The weighing system as claimed in claim 4, wherein said computing server is further configured to allow a user to input the threshold value.

8. The weighing system as claimed in claim 3, further comprising:
a computing server; and
a server-communicating unit disposed in said weight scale, electrically connected to said processor, and configured to be wirelessly connected to said computing server,
wherein said processor is further configured to send the value of intake weight and the value of output weight via said server-communicating unit to said computing server for storage,
wherein said computing server is further configured to calculate a sum of a plurality of values of intake weight that are received from said processor within a preset time period as a value of accumulated intake weight, to calculate a sum of a plurality of values of output weight that are received from said processor within the preset time period as a value of accumulated output weight, to calculate an absolute value of a difference between the value of accumulated intake weight and the value of accumulated output weight as an intake-output difference, to determine whether the intake-output difference is greater than a threshold value, and to output an alert corresponding to a relationship between the value of accumulated intake weight and the value of accumulated output weight when it is determined that the intake-output difference is greater than the threshold value.

9. The weighing system as claimed in claim 8, wherein said processor is further configured to send the value of intake weight and the value of output weight via said server-communicating unit to said computing server for storage.

10. The weighing system as claimed in claim 8, wherein said computing server is further configured to obtain a preset value from an external device as the threshold value.

11. The weighing system as claimed in claim 8, wherein said computing server is further configured to allow a user to input the threshold value.

12. The weighing system as claimed in claim 1, wherein said processor is further configured, when operating in the output mode and receiving the identification number of the subject from said reader again, to:
control said display to display one of the output-type visual symbols that is related to the first value of output-related weight stored in said memory device with respect to the subject;
determine whether the one of said output-type buttons is pressed again; and
when it is determined that the one of said output-type buttons is pressed again, control said display to further display the first value of output-related weight stored in said memory device, and then in response to receipt of another entry of weight data from said weight scale, obtain a second value of output-related weight based on the another entry of weight data, control said display to further display the second value of output-related weight, calculate a difference between the first value of output-related weight and the second value of output-related weight as a value of output weight, and output the value of output weight.

13. The weighing system as claimed in claim 1, further comprising a reader-communicating unit disposed on said weight scale, electrically connected to said processor, and configured to be electrically connected to said reader for receiving the identification number of the subject from said reader and to send the identification number of the subject to said processor.

14. The weighing system as claimed in claim 1, wherein said mode switch is disposed at a back side of said weight scale.

15. The weighing system as claimed in claim 1, wherein said output-type button set and said intake-type button set are spaced apart from each other in a horizontal direction of said weight scale.

16. The weighing system as claimed in claim 1, wherein said output-type button set and said intake-type button set are spaced apart from each other in a vertical direction of said weight scale.

17. The weighing system as claimed in claim 1, further comprising a mobile cart that is configured to support said reader and said weight scale, and to carry said reader and said weight scale to move together with the mobile cart.

18. The weighing system as claimed in claim 1, wherein said reader is a barcode reader.

* * * * *